United States Patent [19]

Csatary

[11] 4,182,321

[45] Jan. 8, 1980

[54] INTRA-UTERINE CONTRACEPTIVE DEVICE

[76] Inventor: Laszlo K. Csatary, 1913 Windsor Rd., Alexandria, Va. 22307

[21] Appl. No.: 855,415

[22] Filed: Nov. 28, 1977

[51] Int. Cl.² ............................................. A61F 5/46
[52] U.S. Cl. .................................. 128/130; 128/260
[58] Field of Search ............... 128/130, 131, 127, 260

[56] References Cited

U.S. PATENT DOCUMENTS 3,995,634  12/1976  Drobish .............................. 128/130

*Primary Examiner*—Lawrence W. Trapp

[57] ABSTRACT

An I.U.D. in which an inner base ring made from a resilient material and formed into a generally circular shape and which carries a jelly-like covering material over its entire extent having formed with a plurality of bead-like protrusions.

8 Claims, 5 Drawing Figures

INTRA-UTERINE CONTRACEPTIVE DEVICE

FIELD OF THE INVENTION

The present invention relates generally to intra-uterine contraceptive devices, known as I.U.D., and more particularly it relates to solid I.U.D having improved physiological effect.

Reference should be had to my concurrently filed co-pending application Ser. No. 855,414 which discloses an I.U.D. having a resilient discontinuous base ring onto which a jelly-like synthetic material is molded having a plurality of bead-like protrusions.

BACKGROUND OF THE INVENTION

I.U.D.'s used for the purpose of contraception are old in art, having been popularized by the development of Dr. Ernst Grafenberg's silver ring. Since that time, almost forty years ago, there have been many improvements in both the configuration and the material of the device as well as the efficiency and the public acceptance of the device. The configuration of the I.U.D.'s most frequently used today may be categorized generally as coils, loops, rings and bows, the best known examples being those devices developed by Margulies, lippes, Ota and Birnberg, respectively.

It has long been recognized that even though I.U.D.'s are safe, reliable and efficient, there are still several very important strucutral aspects that can be improved.

It has been also recognized that although the I.U.D. must be readily removable, if possible without surgical interference, yet it must be capable of resisting expulsion caused by the involuntary uterine contractions exhibited by the fundus muscle. These are, of course, diametrically opposite conditions, but which must nevertheless be met for the I.U.D to be effective.

It has also been recognized that the I.U.D. for proper reliability must have a good contact with the walls of the uterus, which belief lead to the inflatable types such as described in my U.S. Pat. No. 3,933,153 and 3,996,932.

It has been also recognized in my aforementioned patents that contact with the inner walls of the uterus is desirable rather at a plurality of smaller regions than at large surfaces in order to minimize irritations of the inner wall of the uterus and to avoid blockage of the menstrual flow. At the same time an I.U.D. answering the above requirements must retain the last mentioned beneficial properties even under the expulsionary effects of the fundus and in addition assumes a shape which laterally increases its size with respect to the cervix under the last mentioned conditions and reliably prevents thereby its expulsion.

The I.U.D. devices described in my aforementioned patents have superior qualities and improved physiological properties, however, due to their inflatable character, they are sensitive to manufacturing conditions and their insertion requires a rather elaborate inserting device equipped with inflating needle.

SUMMARY OF THE INVENTION

It is, therefore, an object of the present invention to provide an improved and novel I.U.D. device, which has superior physiological characteristics despite its easy manufacturing and can be inserted into the uterus relatively easily and which does not interfere with the normal physiological processes, such as the menstrual flow, of the female body and which is capable of resisting expulsionary forces of the uterus.

It is another object of the present invention to provide an improved and novel I.U.D. device of the above described type which due to its shaping will contact the inner walls of the uterus at a plurality of regions in a resilient manner instead of presenting a large homogeneous surface pressing against the inside of the uterus.

It is still another object of the present invention to provide an improved and novel I.U.D. device of the above type which under the expulsionary forces of the fundus will undergo a change of its shape but it still retains its basic shape having a configuration the smallest dimension of which is still much larger than the opening of the cervix, such change in shape taking place without offering any long straight or hard small surfaces to contact the walls of the uterus.

Briefly, in accordance with the present invention, there is provided a novel I.U.D. having a resilient continuous base ring onto which a jelly-like synthetic material is molded having a plurality of bead-like protrusions.

BRIEF DESCRIPTION OF THE DRAWINGS

The present invention will become more readily apparent from the following description of the preferred embodiments thereof shown in the accompanying drawings, in which.

DESCRIPTION OF THE PREFERRED EMBODIMENTS

Figure 1:
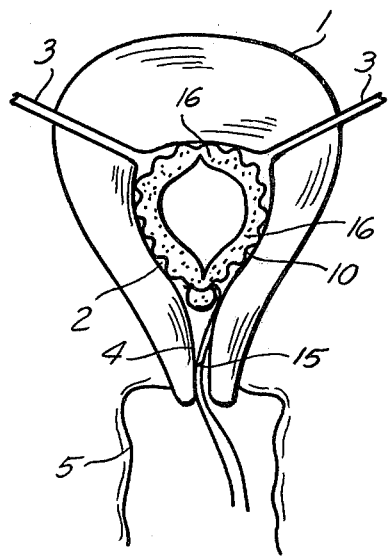
FIG. 1 is a schematic illustration of one of the embodiments of the I.U.D. device according to the present invention in situ within the uterus.
Figure 2:
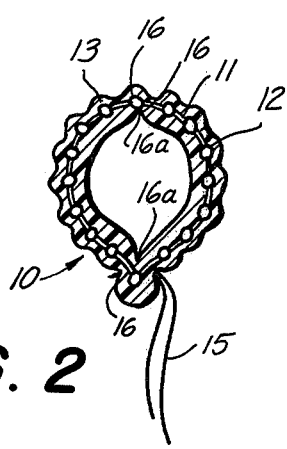
FIG. 2 is an illustration of the I.U.D. device of FIG. 1 in section.
Figure 3:
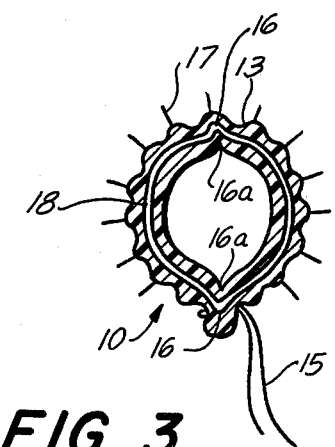
FIG. 3 illustrates an additional embodiment of the I.U.D. device according to the present invention.

With reference to FIGS. 1-3 illustrating the I.U.D. devices according to the present invention, it is noted that FIG. 1 is schematic representation of the uterus 1 and of the adjacent part of the female body, such as the internal part 2 of the uterus 1 which communicates by means of tubes 3 with the ovaries, not shown, and through the cervix 4 with the vagina 5. The first preferred embodiment 10 of the I.U.D. device according to the present invention is illustrated in situ and which has a generally circular shape having the overall diameter between 20-30 mm.

FIG. 2 represents the I.U.D. device as shown in FIG. 1 in more detail and as can be seen in FIGS. 1 and 2, it is generally circular in shape. As can be seen in FIGS. 1 and 2 the structural details of the I.U.D. device according to the present invention include a base ring 11 made form a hard but resilient synthetic material capable of retaining its shape, such as, made from polyethylene and which has the diameter of about 1 mm. It carries on it a plurality of beads 12 and which have a diameter of about 2 mm. As can be seen also in FIGS. 1 and 2 the bead 14 which is the bead at the bottom of the circular shaped base ring 11 is made larger for the purpose of reliably attaching thereto the control cord 15. The base ring 11 with its beads 12 is formed and prestressed to retain its circular shape and, in order when the fundus of the uterus is pressing on it, it should respond to the expulsionary forces of the fundus only to slightly flatten into an elliptical form but still retain the generally circular shape so that the entire device could not be expelled through the cervix 4.

According to the present invention the base ring 11 and the beads 12 thereon are covered with a soft physiologically inert material having a jelly-like consistency, such as silicone rubber or teflonized rubber, in a thickness so that the diameter of the beads 12 with the soft material 13 thereon will be anywhere between 3-5 mm. The beads of material 13 may be formed only on the outside, the inside diameter remaining smooth as shown, or formed on both sides. As the bead 14 has been larger than the other beads, its final diameter with the soft synthetic material thereon will become around 5-6 mm.

Figure 4:
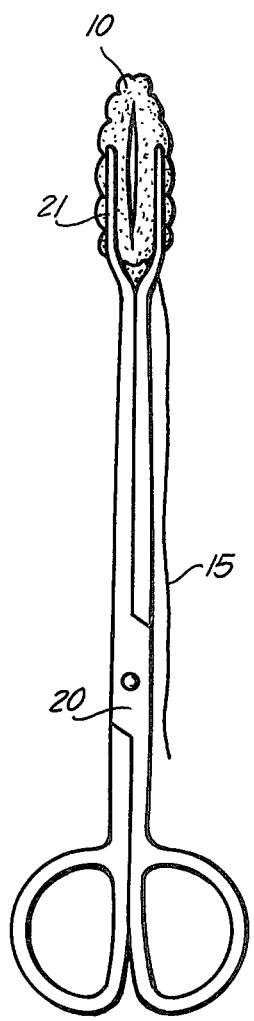
FIGS. 4 and 4a illustrate a known inserting device for use with the embodiments of the I.U.D. devices according to FIGS. 1-3.
Figure 4A:
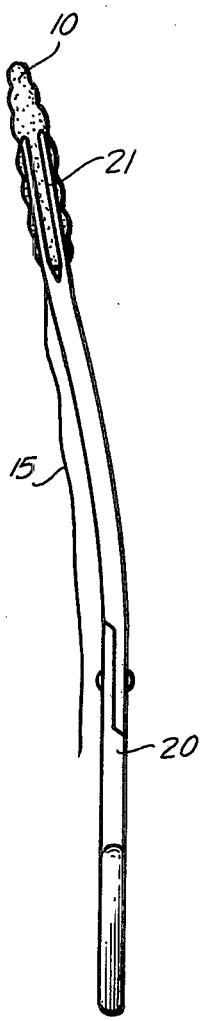

At least the base ring 11 has a pre-formed slight discontinuity 16 in the generally circular shape which points outward and facilitate the squeezing of the I.U.D. to a smaller narrow shape when placed into the insertion device 20 shown in FIGS. 4 and 4a for introduction into the cervix 4. The inside diameter of the soft material may have also such discontinuity 16a.

With reference to FIG. 3 it is noted that the basic shape of the I.U.D. device remains the same except that the base ring 11 has been replaced by a smooth ring-shaped plastic material 18 similarly being shape-retaining and having a large bead 14 at the end thereof to which the control cord 15 is attached. The embodiment of the I.U.D. device 10 according to FIG. 3 includes the further improvement of a plurality of whiskers 17 made from the same soft synthetic material 13 as the beads are made with the additional advantage that the whiskers 17 which are soft and resilient come into contact with the wall of the uterus and have an additional physiological effect on it without the slightest possibility of entering the wall of the uterus due to their softness and resiliency.

With reference to FIGS. 4 and 4a, illustrating an inserting device for the I.U.D. devices 10 illustrated in FIGS. 1-3, it is noted that it is in the form of a surgical scissor 20 made from a plastic material and readily disposable after the I.U.D. has been inserted therewith. The inserting device 20 has a pair of two-forked prongs 21 which when the I.U.D. device 10 is placed inbetween and when the handle of the scissor is squeezed together, will squeeze down the I.U.D. device into an elongated oval shape as illustrated in FIGS. 4 and 4a, and which will not be wider than the normal size of the cervix 4. When the inserting device 20 is inserted together with the I.U.D. device 10 squeezed together in its prongs 21 up into the uterus 2, then it is opened up and the I.U.D. device 10 will pop open and leave the prongs 21 whereupon the inserting device is closed again and removed through the cervix 4 and disposed.

The above inserting device has been disclosed in my aforementioned U.S. patents.

As has been shown, an I.U.D. device has been disclosed which retains all the advantages of my earlier aforementioned U.S. patents, namely, by coming into contact at several points with the walls of the uterus. In addition, it offers sufficient space for the menstrual flow, while at the same time it is capable of offering reliable resistance to the expulsionary forces of the fundus of the uterus 1 by resiliently retaining its circular shape. In addition, the resilient and soft nature of the covering material 13 on the base ring 11 will prevent entry of the device into the wall of the uterus while good physical contact with the uterus wall is retained.

It is within the scope of the ivention to make obvious modifications, such as using a stainless steel wire for the base ring 11. Also there is a great variety of materials available for the covering material 13.

It is also within the scope of the present invention to use the base ring 11 alone as an I.U.D. in which case the dimensions may be simply changed, that is, the size of the beads 12 and the basic frame are enlarged.

I wish it to be understood that I do not desire to be limited to the exact details of construction shown and described, for obvious modifications will occur to a person skilled in the art.

Having thus described the invention, what I claim as new and desire to be secured by Letters Patent, is as follows:

1. An intra-uterine contraceptive device comprising an inner base ring made from a resilient material and formed into a generally circular shape, and a substantially homogeneous jelly-like material formed on said inner ring into a plurality of bead-like protrusions, said protrusions being disposed over the circumferential length of said inner ring.

2. The contraceptive device as claimed in claim 1, wherein said base ring has a plurality of bead-like formations thereon, the bead-shaped protrusions of said covering material coinciding with the bead-like formations of said base ring.

3. The contraceptive device as claimed in claim 2, wherein in the bead-shaped protrusions of said covering material are formed over the peripheral surface of said device, the inner surface of said covering material being a smooth surface.

4. The contraceptive device as claimed in claim 1, wherein said covering material has a plurality of whisker means formed on said bead-like shapes thereof.

5. The contraceptive device as claimed in claim 1, wherein said base ring is made from a synthetic material.

6. The contraceptive device as claimed in claim 1, wherein said covering material is made from silicone rubber or teflonized rubber.

7. The contraceptive device as claimed in claim 1, wherein the jelly-like material covers said inner ring over its entire extent.

8. The contraceptive device as claimed in claim 1, wherein said base ring at opposing locations has at each an indentation formed therein for facilitating insertion of the device into the uterus.

* * * * *